United States Patent
Megati et al.

(10) Patent No.: US 7,671,196 B2
(45) Date of Patent: Mar. 2, 2010

(54) DIAZEPINOQUINOLINES, SYNTHESIS THEREOF, AND INTERMEDIATES THERETO

(75) Inventors: Sreenivasulu Megati, New City, NY (US); Anita Wai-Yin Chan, Fort Lee, NJ (US); Gregg B. Feigelson, Chester, NY (US)

(73) Assignee: Wyeth LLC, Madison, NJ (US)

( * ) Notice: Subject to any disclaimer, the term of this patent is extended or adjusted under 35 U.S.C. 154(b) by 820 days.

(21) Appl. No.: 11/491,590

(22) Filed: Jul. 24, 2006

(65) Prior Publication Data

US 2007/0027142 A1   Feb. 1, 2007

Related U.S. Application Data

(60) Provisional application No. 60/702,509, filed on Jul. 26, 2005.

(51) Int. Cl.
C07D 487/02 (2006.01)
(52) U.S. Cl. .................................................... 540/555
(58) Field of Classification Search .................. 540/555
See application file for complete search history.

(56) References Cited

U.S. PATENT DOCUMENTS

| | | | |
|---|---|---|---|
| 3,158,619 A | 11/1964 | Wagner | |
| 3,235,564 A | 2/1966 | Wagner | |
| 3,296,252 A | 1/1967 | Frey et al. | |
| 3,329,676 A | 7/1967 | Bell et al. | |
| 3,335,134 A | 8/1967 | Frey et al. | |
| 3,417,101 A | 12/1968 | Bell et al. | |
| 3,466,274 A | 9/1969 | DeRidder | |
| 3,714,149 A | 1/1973 | Hester | |
| 3,914,250 A | 10/1975 | Kim | |
| 4,880,814 A | 11/1989 | Chu et al. | |
| 4,948,897 A | 8/1990 | Riggs | |
| 4,997,831 A | 3/1991 | Bays et al. | |
| 5,045,545 A | 9/1991 | Bays et al. | |
| 5,134,127 A | 7/1992 | Stella et al. | |
| 5,376,645 A | 12/1994 | Stella et al. | |
| 5,384,330 A | 1/1995 | Dieter et al. | |
| 5,565,483 A | 10/1996 | Hewawasam et al. | |
| 5,834,454 A | 11/1998 | Kitano et al. | |
| 6,090,803 A | 7/2000 | Failli et al. | |
| 6,096,735 A | 8/2000 | Ogawa et al. | |
| 6,096,736 A | 8/2000 | Ogawa et al. | |
| 6,194,407 B1 | 2/2001 | Failli et al. | |
| 6,414,144 B1 | 7/2002 | Welmaker et al. | |
| 6,503,900 B2 | 1/2003 | Sabb et al. | |
| 6,699,852 B2 | 3/2004 | Robichaud et al. | |
| 6,720,316 B2 | 4/2004 | McWhorter | |
| 6,759,407 B2 | 7/2004 | Goebel et al. | |
| 6,777,405 B2 | 8/2004 | Barton et al. | |
| 6,849,619 B2 | 2/2005 | Robichaud et al. | |
| 6,858,604 B2 | 2/2005 | Sabb et al. | |
| 7,129,237 B2 | 10/2006 | Ramamoorthy | |
| 7,271,162 B2 | 9/2007 | Sabb et al. | |
| 7,271,163 B2 | 9/2007 | Sabb et al. | |
| 7,271,164 B2 | 9/2007 | Sabb et al. | |
| 2002/0055504 A1 | 5/2002 | Chan | |
| 2002/0058689 A1 | 5/2002 | Welmaker et al. | |
| 2002/0062022 A1 | 5/2002 | Sabb et al. | |
| 2002/0086860 A1 | 7/2002 | Sabb et al. | |
| 2002/0107242 A1 | 8/2002 | Sabb et al. | |
| 2002/0119966 A1 | 8/2002 | Sabb et al. | |
| 2002/0128261 A1 | 9/2002 | Sabb et al. | |
| 2002/0147200 A1 | 10/2002 | Nilsson | |
| 2002/0150616 A1 | 10/2002 | Vandecruys | |
| 2002/0183395 A1 | 12/2002 | Argentieri | |
| 2003/0050300 A1 | 3/2003 | McWhorter | |
| 2003/0091505 A1 | 5/2003 | Fu | |
| 2003/0092694 A1 | 5/2003 | Nilsson et al. | |
| 2003/0232814 A1 | 12/2003 | Nilsson et al. | |
| 2004/0009970 A1 | 1/2004 | Ramamoorthy | |
| 2004/0019040 A1 | 1/2004 | Ramamoorthy et al. | |
| 2004/0029949 A1 | 2/2004 | Argentieri | |
| 2004/0034005 A1 | 2/2004 | Gao et al. | |
| 2004/0092502 A1 | 5/2004 | Fevig et al. | |
| 2004/0235856 A1 | 11/2004 | McMurray et al. | |
| 2004/0235859 A1 | 11/2004 | Adams et al. | |
| 2006/0110451 A1 | 5/2006 | Lin | |
| 2006/0111305 A1 | 5/2006 | Tong | |
| 2006/0122385 A1 | 6/2006 | Dehnhardt | |
| 2007/0004707 A1 | 1/2007 | Ramamoorthy | |
| 2007/0027142 A1 | 2/2007 | Megati | |
| 2007/0088022 A1 | 4/2007 | Feigelson | |
| 2007/0167438 A1 | 7/2007 | Rosenzweig-Lipson | |

(Continued)

FOREIGN PATENT DOCUMENTS

EP    0344015    11/1989

(Continued)

OTHER PUBLICATIONS

Wilen et al., "Strategies in optical resolutions," *Tetrahedron* 33:2725 (1977).
Bishop et al., "New 5HT$_{2C}$ receptor agonists," *Expert Opin. Ther. Patent* 13:1691-1705 (2003).
Martin et al., "Activity of Aromatic Substituted Phenylpiperazines Lacking Affinity for Dopamine Binding Sites in a Preclinical Test of Antipsychotic Efficacy," *J. Med. Chem.* 32:1052-1056 (1989).
Browning et al., "The Antipsychotic-like Action of a 5-HT$_{2C}$ Agonist on Conditioned Avoidance Behavior in Rats," *Society for Neuroscience Abstracts* 25(2): Abstract 830.12 (1999).
Hester et al., "Pyrrolo[3,2,1-jk][1,4]benzodiazepines and Pyrrolo[1,2,3-et][1,5]benzodiazepines Which Have Central Nervous System Activity," *J. Med. Chem.* 13: 827-835 (1970).
Kim et al., "Synthesis of 1,2,3,4,8,9,10,11-Octahydro-[1,4]diazepino[6,5,4-jk]carbazole and Related Compounds," *J. Heterocycl. Chem.* 13(6): 1187-1192 (1976).

(Continued)

*Primary Examiner*—Brenda L Coleman
(74) *Attorney, Agent, or Firm*—Doina G. Ene

(57) ABSTRACT

The present invention relates to methods for synthesizing compounds useful as 5HT$_{2C}$ agonists or partial agonists, derivatives thereof, and to intermediates thereto.

4 Claims, No Drawings

U.S. PATENT DOCUMENTS

| | | |
|---|---|---|
| 2007/0225274 A1 | 9/2007 | Jacobson |
| 2007/0225277 A1 | 9/2007 | Rosenzweig-Lipson |
| 2007/0225278 A1 | 9/2007 | Rosenzweig-Lipson |
| 2007/0225279 A1 | 9/2007 | Rosenzweig-Lipson |
| 2007/0238725 A1 | 10/2007 | Rosenzweig-Lipson |
| 2008/0009480 A1 | 1/2008 | Sabb et al. |
| 2009/0093630 A1 | 4/2009 | Megati |

FOREIGN PATENT DOCUMENTS

| | | |
|---|---|---|
| EP | 0357417 | 3/1990 |
| EP | 1714963 | 10/2006 |
| EP | 1792629 | 6/2007 |
| JP | 02-040379 | 2/1990 |
| JP | 10-237073 | 9/1998 |
| JP | 2001-89461 | 4/2001 |
| SU | 930902 | 11/1982 |
| WO | WO-90/15058 | 12/1990 |
| WO | WO-91/11172 | 8/1991 |
| WO | WO-94/02518 | 2/1994 |
| WO | WO-96/29316 | 9/1996 |
| WO | WO-97/30999 | 8/1997 |
| WO | WO-97/31000 | 8/1997 |
| WO | WO-98/55148 | 12/1998 |
| WO | WO-99/41240 | 8/1999 |
| WO | WO-99/66934 | 12/1999 |
| WO | WO-99/67219 | 12/1999 |
| WO | WO-00/35922 | 6/2000 |
| WO | WO-00/40226 | 7/2000 |
| WO | WO-00/64899 | 11/2000 |
| WO | WO-00/76984 | 12/2000 |
| WO | WO-00/77002 | 12/2000 |
| WO | WO-01/12602 | 2/2001 |
| WO | WO-01/12603 | 2/2001 |
| WO | WO-01/64246 | 9/2001 |
| WO | WO-02/08186 | 1/2002 |
| WO | WO-02/36596 | 5/2002 |
| WO | WO-02/42304 | 5/2002 |
| WO | WO-02/059124 | 8/2002 |
| WO | WO-02/059129 | 8/2002 |
| WO | WO 03/091250 A | 11/2003 |
| WO | WO 03/091251 A | 11/2003 |
| WO | WO-03/091257 | 11/2003 |
| WO | WO-03/097636 | 11/2003 |
| WO | 2004072046 | 8/2004 |
| WO | WO-2004/094401 | 11/2004 |
| WO | WO-2005/023243 | 3/2005 |
| WO | 2006052768 | 5/2006 |
| WO | WO-2007/020533 | 2/2007 |

OTHER PUBLICATIONS

Haerter et al., "Schmidt Reaction on Tetrahydro-Quinolone Derivatives," *Chimia* 30: 50-52 (1976).

Lowry et al., "Protein Measurement with the Folin Phenol Reagent," *J. Biol. Chem.* 193: 265-275 (1951).

Naruto et al., "Photocyclization of N-Chloroacetyl Derivatives of Indolylethylamines to Azepinoindoles and Azocinoindoles. Correlation of the Reactivity of Indole Radicals with Frontier Electron Densities Calculated by Unrestricted Hartree-Fock Mo," *Tetrahedron Lett.* 39: 3399-3402 (1975).

Digiovanni et al., "Preferential Modulation of Mesolimbic Vs. Nigrostriatal Dopaminergic Function by Serotonin$_{2C/2B}$ Receptor Agonists: A Combined In Vivo Electrophysiological and Microdialysis Study," *Synapse* 35: 53-61 (2000).

DiMatteo et al., "Selective blockade of serotonin$_{2C/2B}$ receptors enhances dopamine release in the rat nucleus accumbens," *Neuropharmacology* 37: 265-272 (1998).

DiMatteo et al., "SB 242 084, a selective serotonin$_{2C}$ receptor antagonist, increases dopaminergic transmission in the mesolimbic system," *Neuropharmacology* 38: 1195-1205 (1999).

Millan et al., "Serotonin (5-HT)$_{2C}$ receptors tonically inhibit dopamine (DA) and noradrenaline (NA), but not 5-HT, release in the frontal cortex in vivo," *Neuropharmacology* 37: 953-955 (1988).

Masand, "Weight gain associated with psychotropic drugs," *Exp. Opin. Pharmacother.* 1(3): 377-389 (2000).

Allison et al., "Antipsychotic-Induced Weight Gain: A Comprehensive Research Synthesis," *Am. J. Psychiatry* 156(11): 1686-1696 (1999).

Cowen et al., "Hypophagic, Endocrine and Subjective Responses to *m*-Chlorophenylpiperazine in Healthy Men and Women," *Human Psychopharmacology* 10: 385-391 (1995).

Schotte et al., "Risperidone compared with new and reference antipsychotic drugs: in vitro and in vivo receptor binding," *Psychopharmacology* 124: 57-73 (1996).

Fox et al., "Behavioral Effects of 5-HT$_{2C}$ Receptor Antagonism in the Substantia Nigra Zona Reticulata of the 6-Hydroxydopamine-Lesioned Rat Model of Parkinson's Disease," *Experimental Neurology* 151: 35-49 (1998).

Whitaker, "Atypical Antipsychotics: A Modest Advance in Treating Schizophrenia," *Spectrum* 2: 1-12 (2000).

Grinev et al., "Synthesis of New Condensed Heterocycles by the Fischer Method," *Chem. Heterocycl. Compd.* 19(9): 959-961 (1983).

Grinev et al., "Synthesis and Aminomethylation of Derivatives of Pyrazino[3,2,1-*jk*]Carbazole and Diazepeno[3,2,1-*jk*]Carbazole," *Chem. Heterocycl. Compd.* 19(12): 1312-1315 (1983).

Lamanova et al., "Synthesis and Pharmacological Activity of 1,4-Diazepino[3,2,1-hi]-Indoles," *Pharm. Chem. J.* 23(2): 113-115 (1989).

Kim et al., "Derivatives of Tetrahydro-1,4-benzodiazepines as Potential Antihypertensive Agents," *J. Med. Chem.* 20(2): 209-212 (1977).

Toscano et al., "Synthesis and Properties of some Tetracyclic Derivatives of 9*H*-Carbazole, 10,11-Dihydro-5*H*-dibenz[*b,f*]azepine, and 5,11-Dihydrodibenz[*b,e*][1,4]oxazepine," *J. Heterocycl. Chem.* 13: 475-480 (1976).

Katritsky et al., "Synthesis of 3,4,7,8-Tetrahydro-6*H*-pyrido[1,2,3-*et*]-1,5-benzodiazepin-2-(1*H*)-ones via Benzotriazole Methodology," *Synthesis* 10: 1487-1490 (1998).

Gatta et al., "Pirazino(1,2-a)- E 1,4-Diazepino(1,2-a)Indoli," *Edizione Scientifica* 30(8): 631-641 (1975).

Lopes et al., "Synthesis of New Tetracyclic Derivatives of 10H-Phenoxazine, 10,11-Dihydro-5H-Dibenzo[b,f]Azepine and (9)10H-Acridinone Through Isatinic Intermediates," *J. Brazilian Chem. Soc.* 4(1): 34-39 (1993).

Rosenzweig-Lipson et al., "Antiobesity-Like Effects of the Selective 5-HT2C Agonist Way 161503" *FASEB J.* 14: A1321 (2000).

Archer et al., "1-Ethyl-4-(3-tropanyl)-tetrahydro-1H-1,4-benzodiazepine," *J. Am. Chem. Soc.* 79: 5783-5785 (1957).

Cuadro et al., "Synthesis of N-(Aminoethyl)Azoles Under Phase Transfer Catalysis," *Synth. Commun.* 21(4): 535-544 (1991).

Perkin et al., "Dihydropentindole and its Derivatives, Part I," *J. Chem. Soc.* 123: 3242-3247 (1923).

Booth et al., "Synthetic and Stereochemical Investigations of Reduced Cyclic Bases. Part V. The Exhausive Methylation of Some Partially Reduced Cyclic Bases," *J. Chem. Soc.* 158: 2302-2311 (1958).

Cowen et al., Why is dieting so difficult? *Nature* 376: 557 (1995).

Robichaud et al., "Recent Advances in Selective Serotonin Receptor Modulation," *Ann. Rep. Med. Chem.* 35: 11-20 (2000).

Hoyer et al., "International Union of Pharmacology Classification of Receptors for 5-Hydroxytryptamine (Serotonin)," *Pharm. Exp. Ther.* 46(2): 157-203 (1994).

Tecott et al., "Eating disorder and epilepsy in mice lacking 5-HT$_{2C}$ serotonin receptors," *Nature* 374: 542-546 (1995).

Kim, "Improved Syntheses of 1,4-Benzodiazepine-2,5-diones," *J. Heterocycl. Chem.* 12:1323-1324 (1975).

Sabb et al., "Cycloalkyl[*b*][1,4]benzodiazepinoindoles are agonists at the human 5-HT$_{2C}$ receptor," *Bioorg. Med. Chem. Lett.* 14: 2603-2607 (2004).

Herrick-Davis et al., "Inverse Agonist Activity of Atypical Antipsychotic Drugs at Human 5-Hydroxytryptamine2C Receptors," *J. Pharm. Exp. Ther.* 295: 226-232 (2000).

Rosenzweig-Lipson et al., "Antidepressant-like effects of the novel, selective, 5-HT2C receptor agonist WAY-163909 in rodents," *Psychopharmacology* 192: 159-170 (2007).

Dunlop et al., "Pharmacological profile of the 5-HT2C receptor agonist WAY-163909; therapeutical potential in multiple indications," *CNS Drug Reviews* 12: 167-177 (2006).

Bew et al., "Experiments on the Synthesis of Azasteroids. Part II," *J. Chem. Soc.* 1775-1777 (1955).

Chrzanowska et al., "Asymmetric Synthesis of Isoquinoline Alkaloids," *Chem. Rev.* 104: 3341-3370 (2004).

Cox et al., "The Pictet-Spengler Condensation: A New Direction for an Old Reaction," *Chem. Rev.* 95: 1797-1842 (1995).

Cui et al., "Catalytic Homogenous Asymmetric Hydrogenations of Largely Unfunctionalized Alkenes," *Chem. Rev.* 105: 3272-3296 (2005).

Maryanoff et al., "Cyclizations of N-Acyliminium Ions," *Chem. Rev.* 104: 1431-1628 (2004).

Ono et al., "Regioselective Synthesis of 8-Hydroxytetrahydroquinolines by the Cyclization of m-Hydroxyphenethyl Ketone O-2,4-Dinitrophenyloximes," *Chem. Lett.* 5: 437-438 (1998).

Royer et al., "Chiral Heterocycles by Iminium Ion Cyclization," *Chem. Rev.* 104: 2311-2352 (2004).

Rozzel et al., "Preparation of Diastereomeric 2-Deuterio-3-Hydroxy Butyrate. A General Method for Hydrogenation of β-Acyloxy-α,β-Unsaturated Crotonates," *Tetrahedron Lett.* 23: 1767-1770 (1982).

Jaroch et al., "Dihydroquinolines as Novel n-NOS Inhibitors," *Bioorg. Med. Chem. Lett.* 12: 2561-2564 (2002).

Tang et al., "New Chiral Phosphorus Ligands for Enantioselective Hydrogenation," *Chem. Rev.* 103: 3029-3069 (2003).

Pribyla et al., "Solubility of Anthracene in Ternary Methyl tert-Butyl Ether + Alcohol + 2,2,4-Trimethylpentane Solvent Mixtures at 298.15 K," *J. Chem. Eng. Data* 45: 974 (2000).

Chen and Qian, "One-Pot Synthesis Of Tetrahydroquinolines Catalyzed By Dy(OTf)3 in Aqueous Solution," *Synthetic Comm.*, 32: 2543-2548, 2002.

Descamps, et al., "Recherches dans la série des benzofurannes XLII. Synthèse de benzofuryl-2 méthylamines et d'amides d'acides coumaryliques", Chime Therapeutique, 5(3): 169-184, 1970.

Gatta, et al., "Reactions With Anthranilamides. Snythesis of Pyrido[3,2,1-Ij]quinazolines, Pyrido[3,2,1-jk]-1, 4-benzodiazepines and Pyrido[3,2,1-kl]-1, 5- benzodiazcones," *Chimica Ther.*, 7: 480-483, 1972.

Gonzalez, et al., "Pictet-Spengler Type Reactions In 3-arylmethylpiperazine-2, 5-diones. Synthesis of Pyrazinotetrahydroisoquinolines," *Tetrahedron*, 60: 6319-6326, 2004.

Katritzky, et al., "Recent Progress In The Synthesis Of 1,2,3,4-Tetrahydroquinolines," *Tetrahedron*, 52: 15031-15070, 1996.

Posson, et al., "Imino Diels-Alder Reaction: Application to the Synthesis of Diverse Cyclopenta[c]Quinoline Derivatives", *Synlett* 2000, No. 2, 209-12.

Stokker, "Preparation of 1,2,3,4-Tetrahydroisoquinolines Lacking Electron Donating Groups—An Intramolecular Cyclization Complementary To The Pictet-Spengler Reaction," *Tetrahedron Letters*, 37: 5453-5456, 1996.

Zhang, et al., "Pictet-Spengler Reaction In Trifluoroacetic Acid. Large Scale Synthesis Of Pyridoindolobenzodiazepine As An Atypical Antipsychotic Agent," *Tetrahedron Letters*, 36: 8387-8390, 1995.

International Search Report, PCT/US2005/040062, May 30, 2006.

Jacques et al., "Dissociable Compunds and Complexes", Enantimoers, Racemates, and Resolutions,378: 257-259, 1991.

International Search Report, PCT/US2006/028655, date of mailing Jan. 30, 2007.

Written Opinion of International Search Report, PCT/US2006/028655, date of mailing Jan. 30, 2007.

DIAZEPINOQUINOLINES, SYNTHESIS THEREOF, AND INTERMEDIATES THERETO

CROSS-REFERENCE TO RELATED APPLICATIONS

The present application claims priority to U.S. Provisional Application Ser. No. 60/702,509, filed Jul. 26, 2005, the entirety of which is hereby incorporated herein by reference.

FIELD OF THE INVENTION

The present invention relates to methods for synthesizing compounds useful as $5HT_{2C}$ agonists or partial agonists, derivatives thereof, and to intermediates thereto.

BACKGROUND OF THE INVENTION

Schizophrenia affects approximately 5 million people. The most prevalent treatments for schizophrenia are currently the 'atypical' antipsychotics, which combine dopamine ($D_2$) and serotonin (5-$HT_2A$) receptor antagonism. Despite the reported improvements in efficacy and side-effect liability of atypical antipsychotics relative to typical antipsychotics, these compounds do not appear to adequately treat all the symptoms of schizophrenia and are accompanied by problematic side effects, such as weight gain (Allison, D. B., et. al., Am. J. Psychiatry, 156: 1686-1696, 1999; Masand, P. S., Exp. Opin. Pharmacother. I: 377-389, 2000; Whitaker, R., Spectrum Life Sciences. Decision Resources. 2:1-9, 2000).

Atypical antipsychotics also bind with high affinity to 5-$HT_{2C}$ receptors and function as 5-$HT_{2C}$ receptor antagonists or inverse agonists. Weight gain is a problematic side effect associated with atypical antipsychotics such as olozapine and olanzapine, and it has been suggested that 5-$HT_{2C}$ antagonism is responsible for the increased weight gain. Conversely, stimulation of the 5-$HT_{2C}$ receptor is known to result in decreased food intake and body weight (Walsh et. al., Psychopharmacology 124: 57-73, 1996; Cowen, P. J., et. al., Human Psychopharmacology 10: 385-391, 1995; Rosenzweig-Lipson, S., et. al., ASPET abstract, 2000).

Several lines of evidence support a role for 5-$HT_{2C}$ receptor agonism or partial agonism as a treatment for schizophrenia. Studies suggest that 5-$HT_{2C}$ antagonists increase synaptic levels of dopamine and may be effective in animal models of Parkinson's disease (Di Matteo, V., et. al., Neuropharmacology 37: 265-272, 1998; Fox, S. H., et. al., Experimental Neurology 151: 35-49, 1998). Since the positive symptoms of schizophrenia are associated with increased levels of dopamine, compounds with actions opposite to those of 5-$HT_{2C}$ antagonists, such as 5-$HT_{2C}$ agonists and partial agonists, should reduce levels of synaptic dopamine. Recent studies have demonstrated that 5-$HT_{2C}$ agonists decrease levels of dopamine in the prefrontal cortex and nucleus accumbens (Millan, M. J., et. al., Neuropharmacology 37: 953-955, 1998; Di Matteo, V., et. al., Neuropharmacology 38: 1195-1205, 1999; Di Giovanni, G., et. al., Synapse 35: 53-61, 2000), brain regions that are thought to mediate critical antipsychotic effects of drugs like clozapine. However, 5-$HT_{2C}$ agonists do not decrease dopamine levels in the striatum, the brain region most closely associated with extrapyramidal side effects. In addition, a recent study demonstrates that 5-$HT_{2C}$ agonists decrease firing in the ventral tegmental area (VTA), but not in the substantia nigra. The differential effects of 5-$HT_{2C}$ agonists in the mesolimbic pathway relative to the nigrostriatal pathway suggest that 5-$HT_{2C}$ agonists have limbic selectivity, and will be less likely to produce extrapyramidal side effects associated with typical antipsychotics.

SUMMARY OF THE INVENTION

As described herein, the present invention provides methods for preparing compounds having activity as $5HT_{2C}$ agonists or partial agonists. These compounds are useful for treating schizophrenia, schizophreniform disorder, schizoaffective disorder, delusional disorder, substance-induced psychotic disorder, L-DOPA-induced psychosis, psychosis associated with Alzheimer's dementia, psychosis associated with Parkinson's disease, psychosis associated with Lewy body disease, dementia, memory deficit, intellectual deficit associated with Alzheimer's disease, bipolar disorders, depressive disorders, mood episodes, anxiety disorders, adjustment disorders, eating disorders, epilepsy, sleep disorders, migraines, sexual dysfunction, gastrointestinal disorders, obesity, or a central nervous system deficiency associated with trauma, stroke, or spinal cord injury. Such compounds include those of formula I:

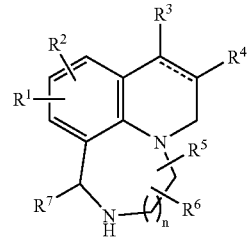

or a pharmaceutically acceptable salt thereof, wherein:
═══ designates a single or double bond;
n is 0, 1, or 2;
$R^1$ and $R^2$ are each independently halogen, —CN, phenyl, —R, —OR, —$C_{1-6}$ perfluoroalkyl, or —$OC_{1-6}$ perfluoroalkyl;
each R is independently hydrogen or a $C_{1-6}$ alkyl group;
$R^3$ and $R^4$ are taken together to form a saturated or unsaturated 4-8 membered ring, wherein said ring is optionally substituted with 1-3 groups independently selected from halogen, —R, or OR;
$R^5$ and $R^6$ are each independently —R; and
$R^7$ is hydrogen or $C_{1-6}$ alkyl.

The present invention also provides synthetic intermediates useful for preparing such compounds.

DETAILED DESCRIPTION OF CERTAIN EMBODIMENTS

The methods and intermediates of the present invention are useful for preparing compounds as described in, e.g. International Patent Application WO 03/091250, in the name of Ramamoorthy, the entirety of which is incorporated herein by reference. In certain embodiments, the present compounds are generally prepared according to Scheme I set forth below:

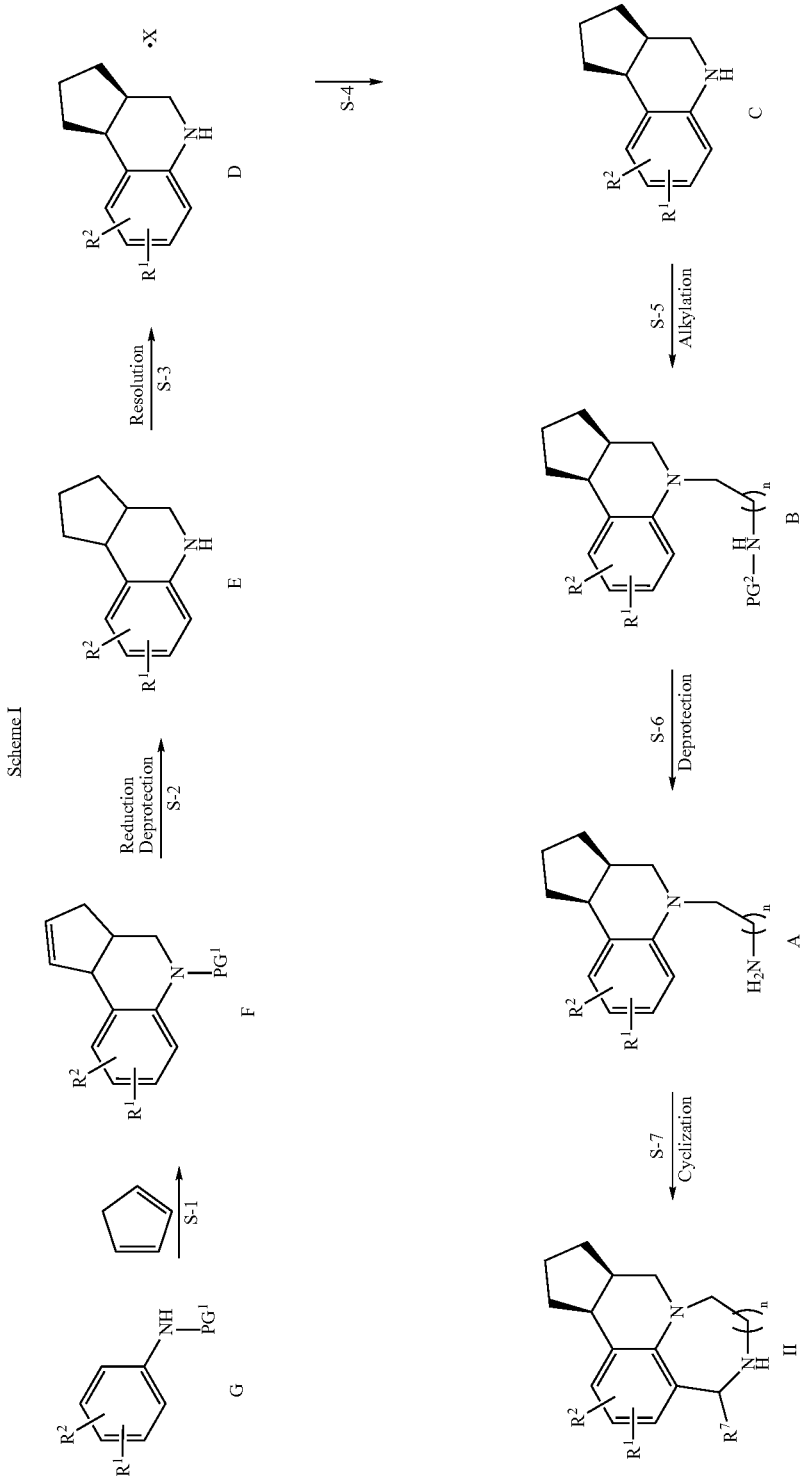

In Scheme I above, each of n, PG$^1$, R$^1$, R$^2$, R$^7$, and PG$^2$ is as defined below and in classes and subclasses as described herein.

In one aspect, the present invention provides methods for preparing chiral quinoline compounds of formula D according to the steps depicted in Scheme 1, above. At step S-1, an aniline of formula G is reacted with formaldehyde, or an equivalent thereof, and cyclopentadiene in the presence of a mineral acid. In certain embodiments, the Diels-Alder reaction of N-benzylaniline and cyclopentadiene in the presence of concentrated HCl provides the cyclopentenyltetrahydroquinoline F, wherein PG$^1$ is benzyl. In other embodiments, step S-1 is performed in a manner substantially similar to that described by Posson, et al, "Imino Diels-Alder Reaction: Application to the Synthesis of Diverse Cyclopenta[c]Quinoline Derivatives" *Synlett* 2000, No. 2, 209-212.

The PG$^1$ group of formulae G and F is a suitable amino protecting group. Suitable amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino protecting groups, taken with the —NH— moiety to which it is attached, include, but are not limited to, aralkylamines, carbamates, allyl amines, amides, and the like. Examples of PG$^1$ groups of formulae G and F include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, benzyl (Bn), fluorenylmethylcarbonyl (Fmoc), acetyl, chloroacetyl, dichloroacetyl, trichloroacetyl, phenylacetyl, trifluoroacetyl, benzoyl, and the like. In other embodiments, the PG$^1$ group of formulae G and F is benzyl.

At step S-2, the olefin of compound F is reduced and the amino group deprotected by removal of PG$^1$. One of ordinary skill in the art would recognize that, depending on the choice of PG$^1$, deprotection and olefin reduction may be performed in the same step. For example, when the PG$^1$ group of formula F is benzyl, reduction of the olefin would simultaneously deprotect the amine group. Accordingly, in certain embodiments, the present invention provides a method of forming a compound of formula E comprising the step of simultaneously reducing the olefin and deprotecting the amino group of formula F. Thus, in certain embodiments, the PG$^1$ group of formula F is an amino protecting group that is removed by reduction, e.g. hydrogenation. For example, reduction of the double bond and deprotection of a benzyl group is achieved in the same reaction by catalytic reduction with Pd-C under a hydrogen atmosphere. In an alternate method, the removal of PG$^1$ and olefin reduction at step S-2 may be performed in a stepwise fashion using methods known to one of ordinary skill in the art.

At step S-3, the racemic compound E is treated with a chiral agent to form a diastereomeric mixture thereof. In certain embodiments, the racemic compound E is treated with a chiral acid to form a diastereomeric salt thereof. The resulting diastereomeric mixture is then separated by suitable means to obtain a compound of formula D. Such suitable means for separating diastereomeric mixtures are well known to one of ordinary skill in the art and include, but are not limited to, those methods described herein. It will be appreciated that, depending upon the chiral acid used, there may be one or more carboxylate moieties present. In certain embodiments, the chiral acid has two carboxylate moieties as with, for example, tartaric acid or a derivative thereof.

Accordingly, one of ordinary skill in the art would appreciate that a compound of formula E may form a hemi salt with said bi-functional chiral acid. As used herein, the term "hemi salt" refers to an adduct having two molecules of a compound of formula E to each molecule of chiral acid. Alternatively, the resulting salt may have a one-to-one mixture chiral acid to a compound of formula E. In certain embodiments, the present invention provides a compound of formula D wherein said compound of formula D comprises equal molar amounts of the chiral acid to an amine of formula E.

In certain embodiments, each of the aforementioned synthetic steps may be performed sequentially with isolation of each intermediate F, E, and D performed after each step. Alternatively, each of steps S-1, S-2, and S-3, as depicted in Scheme I above, may be performed in a manner whereby no isolation of intermediates F and E is performed.

When X is a chiral acid, the compound of formula D, at step S-4, is treated with a suitable base to form the free base compound C. Free bases according to the invention are also prepared, for example, by contacting a compound of formula D with a suitable base in the presence of a solvent suitable for free base formation. Such suitable bases include strong inorganic bases, i.e., those that completely dissociate in water under formation of hydroxide anion. In certain embodiments, the base is added in an amount of at least about 1 mol. eq. and, in other embodiments, in an amount of at least about 1 mol. eq. to about 10 mol. eq. relative to the compound of formula D. Examples of such bases include alkaline metals, alkaline earth metal hydroxides, and combinations thereof. In other embodiments, the suitable base is sodium hydroxide.

Examples of solvents suitable for use during free base formation at step S-4 include polar solvents such as alkyl alcohols, such as C$_1$ to C$_4$ alcohols (e.g. ethanol, methanol, 2-propanol), water, dioxane, or THF (tetrahydrofuran) or combinations thereof. In certain embodiments, the suitable solvent is a C$_1$ to C$_4$ alcohol such as methanol, ethanol, 2-propanol, water, or combination thereof. According to one aspect of the present invention, aqueous sodium hydroxide is used at step S-4. According to another aspect of the present invention, the free base formation at step S-4 is performed in a bi-phasic mixture of solvents whereby the compound of formula C, as it is formed, is extracted into an organic layer. Thus, a suitable bi-phasic mixture of solvents includes an aqueous solvent and a non-miscible organic solvent. Such non-miscible organic solvents are well known to one of ordinary skill in the art and include halogenated hydrocarbon solvents (e.g. methylene chloride and chloroform), benzene and derivatives thereof (e.g. toluene), esters (e.g. ethyl acetate and isopropyl acetate), and ethers (e.g. MTBE, THF and derivatives thereof, glyme, and diglyme) and the like. In certain embodiments, the free base formation at step S-4 is performed in a bi-phasic mixture comprising water and toluene. In other embodiments, the suitable base is water soluble such that the reaction is performed in a mixture of toluene and a suitable aqueous base, such as aqueous sodium hydroxide.

At step S-5, N-alkylation of the chiral compound C affords a compound of formula B. In certain embodiments, this N-alkylation is performed with 2-methyl-2-oxazoline in the presence of catalytic amount of acid to afford the N-acetyl-N-ethylenediamine compound B, wherein n is 1 and PG$^2$ is acetyl.

Removal of the PG$^2$ protecting group of formula B, at step S-6, affords the diamine compound of formula A. In certain embodiments, the PG$^2$ group of formula B is removed by acid hydrolysis. It will be appreciated that upon acid hydrolysis of the PG$^2$ group of formula B, a salt thereof is formed. For example, where the PG$^2$ group of formula B is removed by treatment with an acid such as trifluoroacetic acid, then the resulting diamine compound would be formed as its trifluoroacetic acid salt. One of ordinary skill in the art would recognize that a wide variety of acids are useful for removing amino protecting groups that are acid-labile and therefore a wide variety of salt forms of a compound of formula A are contemplated.

In other embodiments, the PG$^2$ group of formula B is removed by base hydrolysis. One of ordinary skill in the art would recognize that a wide variety of bases are useful for removing amino protecting groups that are base-labile.

At step S-7, a compound of formula A is treated with formaldehyde, or an equivalent thereof, to provide a compound of formula II. In certain embodiments, a compound of formula A is treated with aqueous formaldehyde to provide a compound of formula II. One or ordinary skill in the art would appreciate that substituted formaldehydes may be used at step S-7 to afford a compound of formula IIa:

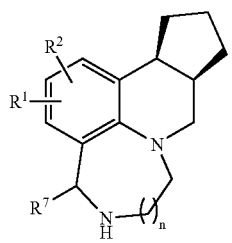

IIa or a pharmaceutically acceptable salt thereof, wherein:
n is 0, 1, or 2;
$R^1$ and $R^2$ are each independently halogen, —CN, phenyl, —R, —OR, —$C_{1-6}$ perfluoroalkyl, or —$OC_{1-6}$ perfluoroalkyl;
each R is independently hydrogen or a $C_{1-6}$ alkyl group; and
$R^7$ is hydrogen or a $C_{1-6}$ alkyl group.

One of ordinary skill in the art will appreciate that a compound of formula II, as prepared by the methods of the present invention, may be treated with a suitable acid to form a salt thereof. In certain embodiments, a compound of formula II is treated with HCl to form the hydrochloride salt thereof.

As used herein, the term "diastereomeric salt" refers to the adduct of a chiral compound of formula E with a chiral acid.

As used herein, the term "enantiomeric salt" refers to the salt of the resolved chiral compound of formula D, wherein said compound of formula D is enriched in one enantiomer. As used herein, the term "enantiomerically enriched", as used herein signifies that one enantiomer makes up at least 80% or 85% of the preparation. In certain embodiments, the term enantiomerically enriched signifies that at least 90% of the preparation is one of the enantiomers. In other embodiments, the term signifies that at least 95% of the preparation is one of the enantiomers.

According to one aspect, the present invention provides a method for preparing a compound of formula II:

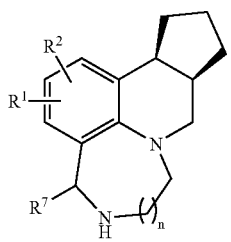

II or a pharmaceutically acceptable salt thereof, wherein:
n is 0, 1, or 2;
$R^1$ and $R^2$ are each independently halogen, —CN, phenyl, —R, —OR, —$C_{1-6}$ perfluoroalkyl, or —$OC_{1-6}$ perfluoroalkyl;
each R is independently hydrogen or a $C_{1-6}$ alkyl group; and
$R^7$ is hydrogen or $C_{1-6}$ alkyl.

As defined generally above, the n group of formula II is 0, 1, or 2. Accordingly, the present invention provides a method for preparing a compound of any of formulae IIa, IIb, or IIc:

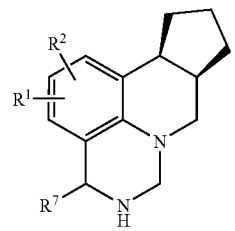

IIa

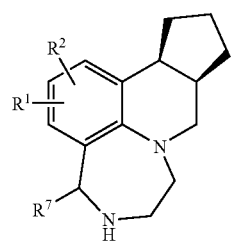

IIb

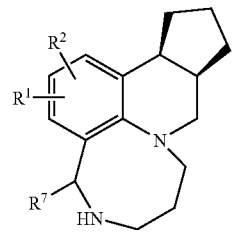

IIc wherein each of $R^1$, $R^2$, $R^7$, and n is as defined above and herein.

According to another aspect, the present invention provides a method for preparing a compound of formula II:

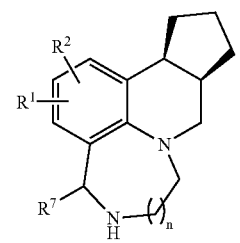

II or a pharmaceutically acceptable salt thereof, wherein:
n is 0, 1, or 2;
$R^1$ and $R^2$ are each independently halogen, —CN, phenyl, —R, —OR, —$C_{1-6}$ perfluoroalkyl, or —$OC_{1-6}$ perfluoroalkyl;
each R is independently hydrogen or a $C_{1-6}$ alkyl group; and
$R^7$ is hydrogen or $C_{1-6}$ alkyl, comprising the steps of:

(a) providing a compound of formula A:

*[Structure A: tricyclic compound with R¹, R² substituents on aromatic ring, fused to cyclopentane, with N-CH₂-(CH₂)ₙ-NH₂ side chain]*

A wherein:

n is 0, 1, or 2;

R¹ and R² are each independently halogen, —CN, phenyl, —R, —OR, —C$_{1-6}$ perfluoroalkyl, or —OC$_{1-6}$ perfluoroalkyl; and each R is independently hydrogen or a C$_{1-6}$ alkyl group, and (b) reacting said compound of formula A with formaldehyde, or an equivalent thereof, to form a compound of formula II.

According to one embodiment, step (b) above is performed using aqueous formaldehyde. In certain embodiments, aqueous formaldehyde is added in an amount sufficient to consume the compound of formula A. In certain embodiments, aqueous formaldehyde is added in amounts of at least about 0.90 mole equivalents, in amounts of about 0.90 mole equivalents to about 1.10 mole equivalents, or in amounts of from about 1.0 mole equivalents to about 1.05 mole equivalents relative to the compound of formula A.

According to another embodiment, step (b) is performed using a formaldehyde equivalent. Such formaldehyde equivalents are well known to one of ordinary skill in the art. In some embodiments, the formaldehyde equivalent is added in solid form to the reaction solvent to form a reaction suspension or the solid formaldehyde equivalent may be suspended in a reaction solvent and added to the reaction mixture. In other embodiments, paraformaldehyde is used as the formaldehyde equivalent, and is added in amounts sufficient to consume the compound of formula A. In some embodiments, parafornaldehyde is added in amounts of at least about 0.90 mole equivalents, in amounts of about 0.90 mole equivalents to about 1.10 mole equivalents, or in amounts of from about 1.0 mole equivalents to about 1.05 mole equivalents relative to the compound of formula A.

In certain embodiments, paraformaldehyde is in a solid form. Paraformaldehyde suitable for the reaction is commercially available in pills (or other granulated forms) and powders from a variety of suppliers such as Aldrich, Fluka, Celanese Chemicals, J. T. Baker, Mallinckrodt Laboratory Chemicals, Miljac Inc., Sego Int. Corp., Spectrum Chemicals Mfg., Total Specialty Chemicals Inc., US Chemicals Inc., Riedel-de Haen, Acros Organics, Pfaltz & Bauer Chemicals, Derivados, Lancaster Synthesis and EM Science. Certain suitable powder forms have at least about 10% particles retained on a 200 mesh screen.

According to another embodiment, the present invention provides a method for preparing a compound of formula A:

A wherein:

n is 0, 1, or 2;

R¹ and R² are each independently halogen, —CN, phenyl, —R, —OR, —C$_{1-6}$ perfluoroalkyl, or —OC$_{1-6}$ perfluoroalkyl; and each R is independently hydrogen or a C$_{1-6}$ alkyl group, comprising the steps of:

(a) providing a compound of formula C:

C wherein:

R¹ and R² are each independently halogen, —CN, phenyl, —R, —OR, —C$_{1-6}$ perfluoroalkyl, or —OC$_{1-6}$ perfluoroalkyl; and each R is independently hydrogen or a C$_{1-6}$ alkyl group, and (b) alkylating said compound of formula C to form a compound of formula B:

B wherein:

n is 0, 1, or 2;

R¹ and R² are each independently halogen, —CN, phenyl, —R, —OR, —C$_{1-6}$ perfluoroalkyl, or —OC$_{1-6}$ perfluoroalkyl;

each R is independently hydrogen or a C$_{1-6}$ alkyl group; and

PG² is a suitable amino protecting group, and (c) deprotecting said compound of formula B to form said compound of formula A.

In certain embodiments, the alkylation at step (b) above is achieved by reacting said compound of formula C with a compound of formula

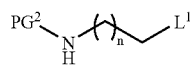

wherein said reaction is performed in a suitable medium and wherein:

n is 0, 1, or 2;

$PG^2$ is a suitable amino protecting group; and $L^1$ is a suitable leaving group.

As defined above, $L^1$ is a suitable leaving group. Suitable leaving groups are well known in the art, e.g., see, "Advanced Organic Chemistry," Jerry March, $5^{th}$ Ed., pp. 351-357, John Wiley and Sons, N.Y. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, and diazonium moieties. Examples of suitable leaving groups include chloro, iodo, bromo, fluoro, methanesulfonyl (mesyl), tosyl, triflate, nitro-phenylsulfonyl (nosyl), and bromo-phenylsulfonyl (brosyl). In certain embodiments, $L^1$ is halogen. In other embodiment, $L^1$ is an optionally substituted alkylsulphonyloxy, optionally substituted alkenylsulfonyloxy, or optionally substituted arylsulfonyloxy group.

According to an alternate embodiment, the suitable leaving group may be generated in situ within the reaction medium. For example, the $L^1$ moiety may be generated in situ from a precursor of that compound of formula

wherein said precursor contains a group readily replaced by $L^1$ in situ. Such an in situ generation of a suitable leaving group is well known in the art, e.g., see, "Advanced Organic Chemistry," Jerry March, pp. 430-431, $5^{th}$ Ed., John Wiley and Sons, N. Y.

In certain embodiments, said alkylation reaction is optionally performed in the presence of a suitable base. One of ordinary skill would recognize that the displacement of a leaving group by an amino moiety is achieved either with or without the presence of a suitable base. Such suitable bases are well known in the art and include organic and inorganic bases.

A suitable medium is a solvent or a solvent mixture that, in combination with the combined compounds, may facilitate the progress of the reaction therebetween. The suitable solvent may solubilize one or more of the reaction components, or, alternatively, the suitable solvent may facilitate the agitation of a suspension of one or more of the reaction components. Examples of suitable solvents useful in the present invention are a protic solvent, a halogenated hydrocarbon, an ether, an ester, an aromatic hydrocarbon, a polar or a non-polar aprotic solvent, or any mixtures thereof. Such mixtures include, for example, mixtures of protic and non-protic solvents such as benzene/methanol/water; benzene/water; DME/water, and the like.

These and other such suitable solvents are well known in the art, e.g., see, "Advanced Organic Chemistry", Jerry March, $5^{th}$ edition, John Wiley and Sons, N.Y.

As defined generally above, the $PG^2$ group of formula B is a suitable amino protecting group. Suitable amino protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Suitable amino protecting groups, taken with the —NH— moiety to which it is attached, include, but are not limited to, aralkylamines, carbamates, allyl amines, amides, and the like. Examples of $PG^2$ groups include t-butyloxycarbonyl (BOC), ethyloxycarbonyl, methyloxycarbonyl, trichloroethyloxycarbonyl, allyloxycarbonyl (Alloc), benzyloxycarbonyl (CBZ), allyl, benzyl (Bn), fluorenylmethylcarbonyl (Fmoc), acetyl, chloroacetyl, dichloroacetyl, trichloroacetyl, phenylacetyl, trifluoroacetyl, benzoyl, and the like. In other embodiments, $PG^2$ group is acetyl, chloroacetyl, dichloroacetyl, trichloroacetyl, phenylacetyl, or trifluoroacetyl. In still other embodiments, the amino protecting group is acetyl.

According to yet another embodiment, one or more reagents may perform as the suitable solvent. For example, an organic base such as triethylamine or diisopropylethylamine, if utilized in said reaction, may serve as the solvent in addition to its role as a basifying reagent.

In other embodiments, the alkylation at step (b) above is achieved by reacting said compound of formula C with

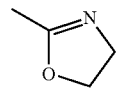

in the presence of a suitable acid to form a compound of formula B wherein n is 1 and $PG^2$ is acetyl. Such suitable acids are well known in the art and include inorganic acids, e.g. hydrochloric acid, hydrobromic acid, phosphoric acid, nitric acid, sulfuric acid or perchloric acid, or organic acids, e.g. acetic acid, oxalic acid, maleic acid, tartaric acid, citric acid, succinic acid, malonic acid, lower alkyl sulfonic acids or aryl sulfonic acids. In certain embodiments, the alkylation at step (b) above is achieved by reacting said compound of formula C with

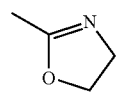

in the presence of toluenesulfonic acid.

Yet another aspect of the present invention provides a method for preparing a compound of formula D:

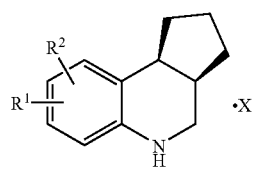

wherein:
$R^1$ and $R^2$ are each independently halogen, —CN, phenyl, —R, —OR, —$C_{1-6}$ perfluoroalkyl, or —$OC_{1-6}$ perfluoroalkyl;

each R is independently hydrogen or a $C_{1-6}$ alkyl group; and

X is a chiral agent, comprising the steps of:
(a) providing a compound of formula E:

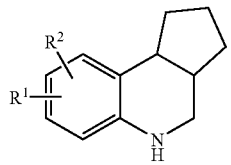

E wherein:
R$^1$ and R$^2$ are each independently halogen, —CN, phenyl, —R, —OR, —C$_{1-6}$ perfluoroalkyl, or —OC$_{1-6}$ perfluoroalkyl; and
each R is independently hydrogen or a C$_{1-6}$ alkyl group, and
(b) treating said compound of formula E with a chiral agent to form a compound of formula D-1:

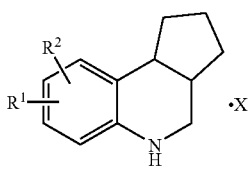

D-1 wherein:
R$^1$ and R$^2$ are each independently halogen, —CN, phenyl, —R, —OR, —C$_{1-6}$ perfluoroalkyl, or —OC$_{1-6}$ perfluoroalkyl;
each R is independently hydrogen or a C$_{1-6}$ alkyl group; and
X is a chiral agent, and
(c) obtaining said compound of formula D by suitable physical means.

The term "chiral agent" refers to an enantiomerically enriched group which may be ionically or covalently bonded to the nitrogen of a compound of formula E. As used herein, the term "enantiomerically enriched", as used herein signifies that one enantiomer makes up at least 85% of the preparation. In certain embodiments, the term enantiomerically enriched signifies that at least 90% of the preparation is one of the enantiomers. In other embodiments, the term signifies that at least 95% of the preparation is one of the enantiomers.

Chiral agents which are ionically bonded to said nitrogen include chiral acids. When the chiral agent is a chiral acid, the acid forms a diastereomeric salt with the nitrogen. The resulting diastereomers are then separated by suitable physical means. Examples of chiral acids include, but are not limited to, tartaric acid and tartaric acid derivatives, mandelic acid, malic acid, camphorsulfonic acid, and Mosher's acid, among others. In certain embodiments, the chiral acid is ditoluoyl-D-tartaric acid. In other embodiments, the chiral acid is ditoluoyl-L-tartaric acid. Chiral agents which may be covalently bonded to the nitrogen are known in the art.

The term "separated by suitable physical means" refers to methods of separating enantiomeric or diastereomeric mixtures. Such methods are well known in the art and include preferential crystallization, distillation, and trituration, among others. Chiral agents and separation methods are described in detail in Stereochemistry of Organic Compounds, Eliel, E. L. and Wilen, S. H., 1994, published by John Wiley and Sons.

In certain embodiments, a chiral salt of formula D is obtained via preferential crystallization of a diastereomeric salt formed at step (b) above. In other embodiments, the crystallization is achieved from a protic solvent. In still other embodiments, the protic solvent is an alcohol. It will be appreciated that the crystallization may be achieved using a single protic solvent or a combination of one or more protic solvents. Such solvents and solvent mixtures are well known to one of ordinary skill in the art and include one or more straight or branched alkyl alcohols. In certain embodiments, the crystallization is achieved from isopropyl alcohol.

In certain embodiments, the chiral salt of formula D comprises an equimolar amount of chiral acid and amine. In other embodiments, the chiral salt of formula D comprises a substoichiometric amount of chiral acid. As used herein, the term "substoichiometric amount" denotes that the chiral acid is used in less than 1 mole equivalent relative to the compound of formula E. In certain embodiments the chiral acid is employed in less than 0.98 mole equivalents. In other embodiments the amine base is employed in less than 0.95 mole equivalents.

It should be readily apparent to those skilled in the art that enantiomeric enrichment of one enantiomer in the crystallized compound D causes an enantiomeric enrichment in the mother liquor of the other enantiomeric form. Therefore, according to another embodiment, the invention relates to a method of enhancing the % ee of a racemic or enantiomerically enriched compound of formula D as compared with a compound of formula D-1. As used herein, the term "% ee" refers to the percent enantiomeric excess as would be understood by one of ordinary skill in the art.

In another preferred embodiment, the crystallized compound D is optionally subjected to an additional crystallization step to cause crystallization and further enrichment of the depicted enantiomer.

According to another embodiment, the present invention provides a method of obtaining an enantiomerically enriched compound of formula D:

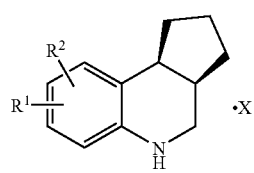

D wherein:
R$^1$ and R$^2$ are each independently halogen, —CN, phenyl, —R, —OR, —C$_{1-6}$ perfluoroalkyl, or —OC$_{1-6}$ perfluoroalkyl;
each R is independently hydrogen or a C$_{1-6}$ alkyl group; and
X is a chiral agent, comprising the steps of:

(a) combining a compound of formula D-1:

D-1 wherein:

R¹ and R² are each independently halogen, —CN, phenyl, —R, —OR, —$C_{1-6}$ perfluoroalkyl, or —$OC_{1-6}$ perfluoroalkyl;

each R is independently hydrogen or a $C_{1-6}$ alkyl group; and

X is a chiral agent, with a suitable solvent and heating to form a solution thereof; and (b) allowing said solution to cool to cause crystallization of an enantiomerically enriched compound of formula D.

In certain embodiments, the suitable solvent utilized in step (a) above is a protic solvent. In still other embodiments, the protic solvent is an alcohol. It will be appreciated that the crystallization may be achieved using a single protic solvent or a combination of one or more protic solvents. Such solvents and solvent mixtures are well known to one of ordinary skill in the art and include one or more straight or branched alkyl alcohols. In certain embodiments, the crystallization is achieved using a mixture of methanol and isopropyl alcohol.

In certain embodiments, the present invention provides a compound of formula D-1:

D-1 wherein:

R¹ and R² are each independently halogen, —CN, phenyl, —R, —OR, —$C_{1-6}$ perfluoroalkyl, or —$OC_{1-6}$ perfluoroalkyl;

each R is independently hydrogen or a $C_{1-6}$ alkyl group; and

X is a chiral agent.

According to another embodiment, the present invention provides a compound of either of formulae D-1 and D-2:

D-1

D-2 wherein each R¹, R² and X is as defined above and in classes and subclasses defined above and herein.

According to one embodiment, the R¹ and R² groups of formulae D-1 and D-2 are each independently an R group. According to another embodiment, one of R¹ and R² is hydrogen. According to yet another embodiment, both of R¹ and R² are hydrogen.

In certain embodiments, the X group of formulae D-1 and D-2 is a chiral acid, thus forming a chiral salt. In other embodiments, the X group of formulae D-1 and D-2 is a tartaric acid derivative. In still other embodiments, the X group of formulae D-1 and D-2 is ditoluoyl-D-tartaric acid.

Yet another embodiment provides a compound of formula D:

D wherein:

R¹ and R² are each independently halogen, —CN, phenyl, —R, —OR, —$C_{1-6}$ perfluoroalkyl, or —$OC_{1-6}$ perfluoroalkyl;

each R is independently hydrogen or a $C_{1-6}$ alkyl group; and

X is a chiral agent.

According to one embodiment, the R¹ and R² groups of formula D are each independently an R group. According to another embodiment, one of R¹ and R² is hydrogen. According to yet another embodiment, both of R¹ and R² are hydrogen.

In certain embodiments, the X group of formula D is a chiral acid, thus forming a chiral salt. In other embodiments, the X group of formula D is a tartaric acid derivative. In still other embodiments, the X group of formula D is ditoluoyl-D-tartaric acid.

According to another embodiment, the present invention provides a compound of formula D, wherein R¹ and R² are both hydrogen and said compound is of formula D-3:

D-3

In certain embodiments, a compound of formula D-3 is provided substantially free of the corresponding enantiomer. "Substantially free," as used herein, means that the compound is made up of a significantly greater proportion of one enantiomer. In other embodiments, at least about 95% by weight of a desired enantiomer is present. In still other embodiments of the invention, at least about 99% by weight of a desired enantiomer is present. Such enantiomers may be isolated from racemic mixtures by any method known to those skilled in the art, including high performance liquid chromatography (HPLC) and chiral salt resolution, or prepared by methods described herein.

Yet another aspect of the present invention provides a method for preparing a compound of formula D:

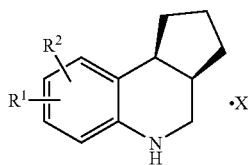

D wherein:
$R^1$ and $R^2$ are each independently halogen, —CN, phenyl, —R, —OR, —$C_{1-6}$ perfluoroalkyl, or —$OC_{1-6}$ perfluoroalkyl;
each R is independently hydrogen or a $C_{1-6}$ alkyl group; and
X is a chiral agent, as described above and herein, wherein said method further comprises the step of treating said compound of formula D with a suitable base to form the free-base compound of formula C:

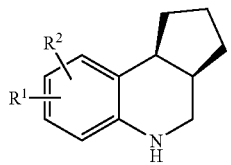

C wherein:
$R^1$ and $R^2$ are each independently halogen, —CN, phenyl, —R, —OR, —$C_{1-6}$ perfluoroalkyl, or —$OC_{1-6}$ perfluoroalkyl; and
each R is independently hydrogen or a $C_{1-6}$ alkyl group.

As used herein, the suitable base is an organic or inorganic base. Such suitable bases include strong inorganic bases, i.e., those that completely dissociate in water under formation of hydroxide anion. In certain embodiments, the base is added in an amount of at least about 1 mol. eq. and, in other embodiments, in an amount of at least about 1 mol. eq. to about 10 mol. eq. relative to the compound of formula D. Examples of such bases include alkaline metals, alkaline earth metal hydroxides, and combinations thereof. In other embodiments, the suitable base is sodium hydroxide.

According to one embodiment, the free base formation is performed in the presence of a suitable solvent. Examples of solvents suitable for use during the free base formation include polar solvents such as alkyl alcohols, such as $C_1$ to $C_4$ alcohols (e.g. ethanol, methanol, 2-propanol), water, dioxane, or THF (tetrahydrofuran) or combinations thereof. In certain embodiments, the suitable solvent is a $C_1$ to $C_4$ alcohol such as methanol, ethanol, 2-propanol, water, or combination thereof. According to one aspect of the present invention, the suitable base is aqueous sodium hydroxide and, thus, the solvent is water.

According to another aspect of the present invention, the free base formation is performed in a bi-phasic mixture of solvents whereby the compound of formula C, as it is formed, is extracted into an organic layer. Thus, a suitable bi-phasic mixture of solvents includes an aqueous solvent and a non-miscible organic solvent. Such non-miscible organic solvents are well known to one of ordinary skill in the art and include halogenated hydrocarbon solvents (e.g. methylene chloride and chloroform), benzene and derivatives thereof (e.g. toluene), esters (e.g. ethyl acetate and isopropyl acetate), ethers (e.g. MTBE, THF and derivatives thereof, glyme, and diglyme), and the like. In certain embodiments, the free base formation is performed in a bi-phasic mixture comprising water and toluene. In other embodiments, the suitable base is water soluble such that the reaction is performed in a mixture of toluene and a suitable aqueous base, such as aqueous sodium hydroxide.

In certain embodiments, the present invention provides a compound of formula III:

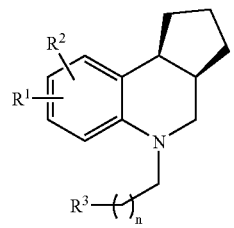

III or a salt thereof, wherein:
n is 0, 1, or 2;
$R^1$ and $R^2$ are each independently halogen, —CN, phenyl, —R, —OR, —$C_{1-6}$ perfluoroalkyl, or —$OC_{1-6}$ perfluoroalkyl;
each R is independently hydrogen or a $C_{1-6}$ alkyl group; and
$R^3$ is $NH_2$ or a suitably protected amino group.

In certain embodiments, the $R^1$ and $R^2$ groups of formula I are each R. In other embodiments, one of $R^1$ and $R^2$ is hydrogen. In still other embodiments, both of $R^1$ and $R^2$ are hydrogen.

Suitable amino protecting groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference. Suitably protected amino groups of $R^3$ include, but are not limited to, aralkylamines, carbamates, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, benzyl (Bn), fluorenylmethylcarbonyl (Fmoc), acetyl, chloroacetyl, dichloroacetyl, trichloroacetyl, phenylacetyl, trifluoroacetyl, benzoyl, and the like. In other embodiments, the amino protecting group is acetyl, chloroacetyl, dichloroacetyl, trichloroacetyl, phenylacetyl, or trifluoroacetyl. In still other embodiments, the amino protecting group is acetyl.

In certain embodiments, the present invention provides a compound of formula IIa or IIc, or a pharmaceutically acceptable salt thereof:

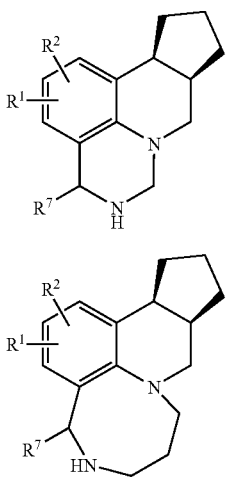

wherein each of $R^1$, $R^2$, and $R^7$ is defined above and herein.

In certain embodiments, the present invention provides a compound of formula IIa wherein $R^1$, $R^2$, and $R^7$ are all hydrogen.

In other embodiments, the present invention provides a compound of formula IIc wherein $R^1$, $R^2$, and $R^7$ are all hydrogen.

Pharmaceutically acceptable salts, including mono- and bi-salts, are those derived from such organic and inorganic acids such as, but not limited to acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

EXAMPLES

As indicated herein, the % ee data was obtained via the following chiral HPLC method:
Column: Chiralcel OD 4.6×250
Mobile Phase: Hexane:IPA:MeOH:TEA 800:10:10:0.5
Flow rate: 1 mL/minute
Temperature: Ambient
Time: 12 minutes
Wavelength: 210 nm As indicated herein, the % purity data was obtained via the following chiral HPLC method:
Column: Chromolith Performance RP-18e (100×4.6 mm)
Mobile Phase: A=95:5:0.1 water:$CH_3CN$:$H_3PO_4$
B=95:5:0.1 $CH_3CN$:water:$H_3PO_4$
Gradient: 5% B to 95% B over 8 minutes
Flow rate: 1 mL/minute
Temperature: Ambient
Time: 10 minutes
Wavelength: 210 nm Example 1

Method A 2,3,3a,4,5,9b-Hexahydro-1H-cyclopenta(c)quinoline:

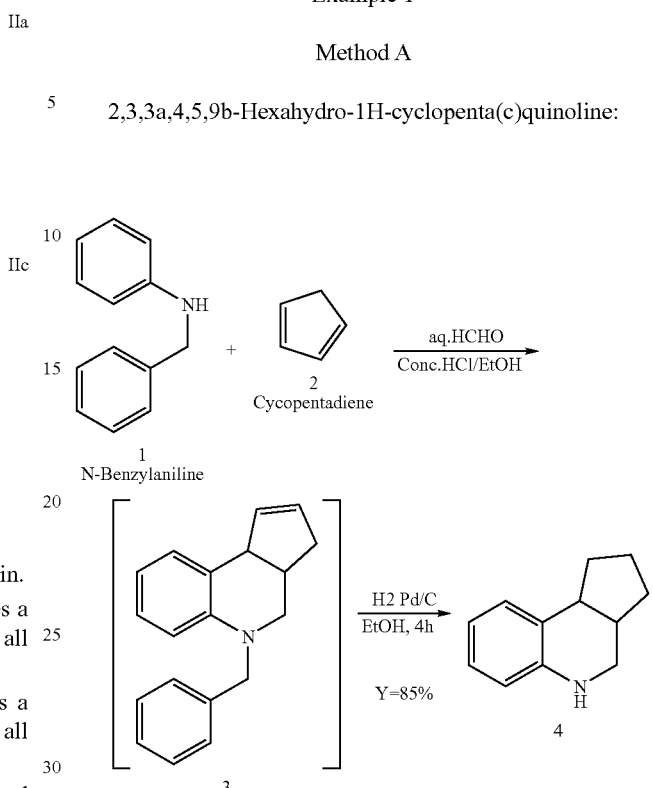

N-phenylbenzylamine hydrochloride (2.0 g) in 20 mL MeOH was cooled to ~5° C. Freshly cracked cyclopentadiene (1.2 g, from atmospheric heating/distillation of dicyclopentadiene) was added to the solution followed by aqueous formaldehyde (37%, 1.04 g). The reaction temperature was maintained at 5-10° C. overnight (ca. 18 hrs). No starting material was observed by TLC (10% ethyl acetate in hexanes). The reaction was then allowed to warm to RT. The reaction was diluted with EtOAc and washed with 0.5N NaOH solution, and then brine. Concentration of the organics gave 2.32 g of crude tricyclic product as an oil. The crude oil from above in 20 mL 1:1 EtOH:EtOAc was treated with 0.175 mL 1N HCl in EtOH and then 5% Pd-C (0.250 g, 50% wet). The mixture was shaken under 40-45 psi $H_2$ overnight. The solids were removed by filtration through celite and the pad is rinsed with EtOAc. The filtrate was concentrated to give a peach colored oil which crystallized under vacuum to give 1.38 g (87%) debenzylated product.

(−)2,3,3a,4,5,9b-Hexahydro-1H-cyclopenta(c)quinoline di-p-toluoyl-D-tartaric acid (6):

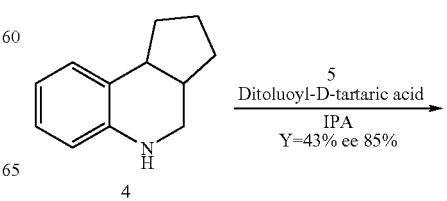

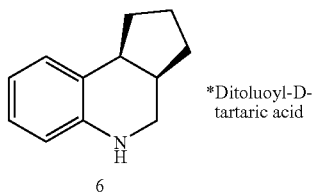

*Ditoluoyl-D-tartaric acid

6

A mixture of the racemic amine (16.0 g, 92.3 mmol), di-p-toluoyl-D-tartaric acid (23.3 g, 60.3 mmol) in IPA (160 mL) was heated to 70° C. for 10-15 minutes. The solids dissolved during this time. The solution was cooled to 0-5° C. over 3 hours. The resulting solids were filtered, washed with cold IPA (60 mL), and dried at 40° C. to give 21.0 g (40%) of the salt as an off-white solid. Chiral HPLC: 85% ee; $^1$H NMR (d6-DMSO) δ 7.91 (d, J=6 Hz, 4H), 7.40 (d, J=6 Hz, 4H), 6.97 (d, J=6 Hz, 1H), 6.84 (t, J=6 Hz, 1H), 6.4-6.6 (m, 2H), 5.83 (s, 2H), 2.9-3.1 (m, 2H), 2.8-3.1 (m, 1H), 2.8-2.9 (m, 1H), 2.5-2.7 (m, 1H), 2.5 (m, 1H), 2.3-2.5 (s, 6H), 2.0-2.2 (m, 3H), 1.8-2.0 (m, 1H), 1.2-1.7 (m, 4H); $^{13}$C NMR (d6-DMSO) δ 167.6, 165.0, 145.7, 144.9, 129.9, 129.8, 129.7, 126.2, 125.2, 116.4, 114.4, 71.7, 43.6, 40.7, 35.8, 35.4, 29.3, 23.0, 21.6.

Example 2

Method B (−)2,3,3a,4,5,9b-Hexahydro-1H-cyclopenta(c)quinoline di-p-toluoyl-D-tartaric acid (6:

In an alternative method, N-phenylbenzylamine (50 g) in 250 mL MeOH was stirred mechanically until dissolved. 29 mL conc. HCl was added in a single portion. The mixture was allowed to cool to RT. The amine HCl salt gradually came out of solution. The suspension was cooled in ice to about 15° C. and the freshly distilled cyclopentadiene [29.4 g, cyclopentadiene is obtained by thermal cracking of dicyclopentadiene via atmospheric short path distillation (pot temperature 165-170° C., distillate ca. 60-70° C.). The cyclopentadiene was collected into an ice-cooled receiver] was added in a single portion. The temperature was allowed to drop back to 15° C. before proceeding, if necessary. Formaldehyde solution (37% aqueous) in 150 mL MeOH was added dropwise so as to maintain an internal temperature of 15-25° C. (15 mins addition time). A yellow solution resulted. Once the addition was complete, the reaction was allowed to stir at RT overnight under nitrogen (12-18 h). The solution was clear, but greenish. The solution was transferred to a 2 L Parr bottle and treated with 1.5 g 10% Pd/C (50% wet) and shaken under 45 psi hydrogen until uptake ceased. Once complete, the mixture was purged with nitrogen and treated with sodium bicarbonate (58 g). The slurry was stirred until the solution was neutral to slightly basic by damp pH paper. The mixture was then filtered through 1 cm celite and the pad rinsed with MeOH (50 mL). The filtrate was concentrated in vacuo and 450 mL IPA added. The mixture was stirred overnight and the resulting solids filtered and rinsed with 50 ml IPA. To the filtrate obtained above was added di-p-toluoyl-D-tartaric acid (63.3 g) in a single portion. The slurry was heated to ca. 80° C. to dissolve all solids. The mixture was then allowed to gradually cool to RT and stir for 3 or more hours. The mixture was then cooled to 0-5° C. in ice and stirred at this temperature for 1-2 hours. The solids were filtered and washed with 100 mL of cold IPA. The faintly blue-green solids were dried in vacuo to afford the title compound. Yield: 46.7 g (31%) Chiral purity (HPLC): 95:5% ee.

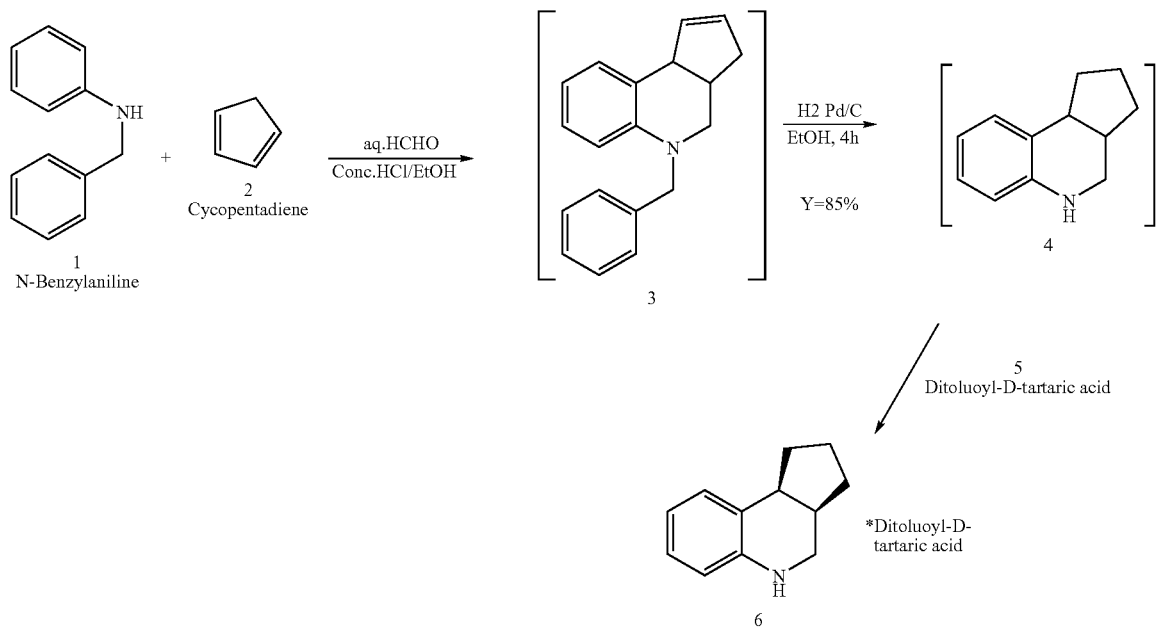

Example 3

(−)2,3,3a,4,5,9b-Hexahydro-1H-cyclopenta(c)quinoline (7):

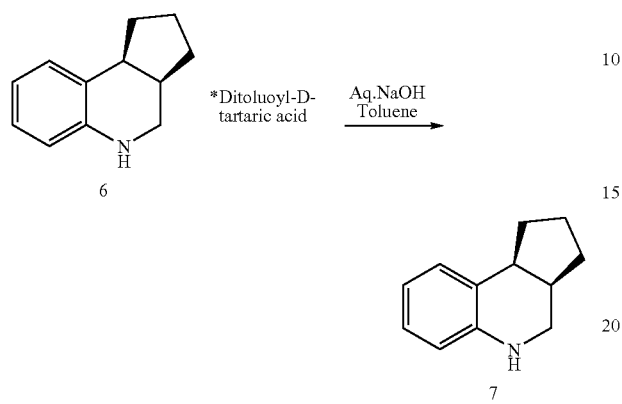

To a suspension of the ditoluoyl-D-tartrate salt (20.67 g, 37 mmol) in toluene (93 mL), aq. NaOH (12 mL of 30% NaOH diluted to 100 mL with water) was added over 5 min. The two-phase mixture was stirred vigorously and the solids slowly dissolved. The two layers were separated. The aqueous layer was extracted with toluene (46 mL). The combined organic layers were concentrated to give 6.4 g (100% yield) of the free base as yellow oil. $^1$H NMR (CDCl$_3$) δ 7.09 (d, J=7.5 Hz, 1H), 6.9-7.0 (m, 1H), 6.6-6.7 (m, 1H), 6.4-6.5 (m, 1H), 3.85 (bs, 1NH), 2.9-3.2 (m, 2H), 2.8-3.1 (m, 1H), 2.80 (t, J=10.3 Hz, 1H), 2.3-2.4 (m, 1H), 2.0-2.2 (m, 1H), 1.8-2.1 (m, 1H), 1.3-1.8 (m, 4H).

Example 4

(−)[2-(1,2,3,3a,4,9b-Hexahydro-cyclopenta[c]quinolin-5-yl)-ethylamine trifluoroacetic acid salt (10):

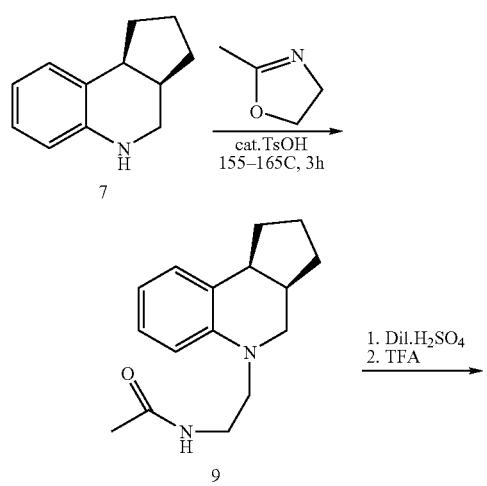

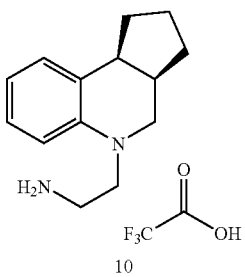

A mixture of amine (6.4 g, 36.9 mmol) and a catalytic amount of p-toluenesulfonic acid (0.07 g, 0.37 mmol) was heated to 165° C. Added 2-methyl-2-oxazoline slowly over 2 h to the reaction mixture at 165° C. Cooled the reaction mixture to 60° C. and then added dil. H$_2$SO$_4$ (6 ml of conc. H$_2$SO$_4$ and 26 mL of water). Stirred for 1 h at 60° C. Cooled to RT, added toluene (40 mL) and 30% NaOH (30 mL). Filter off the solids and wash it with toluene (2×10 mL). Each wash was used to extract the aqueous layer. Washed the combined organic extracts with water (25 mL). Concentrate the toluene layer to 20 mL volume and cooled to 10° C. Added a solution of trifluoroacetic acid (2.4 mL, 31.2 mmol) in toluene (7.5 mL) over 15 min. Stirred for 2 h at 10° C. It was filtered and washed with toluene (10 mL). Dried the TFA salt at 55° C. in a vacuum oven. 7.7 g (yield 63%) HPLC 97.6% Chiral Purity 92.2:7.8.

Example 5

(−)-4,5,6,7,9,9a,10,11,12,12a-decahydrocyclopenta[c][1,4]diazepino[6,7,1-ij]quinoline hydrochloride (12):

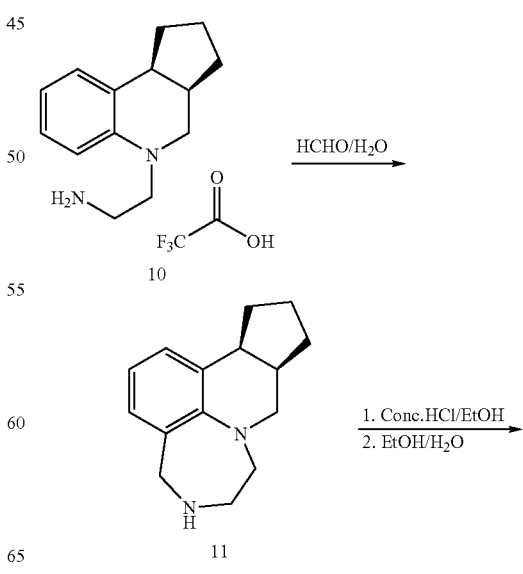

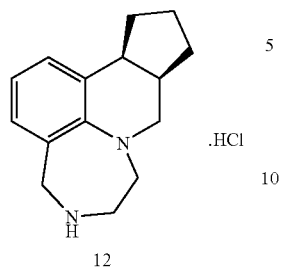

.HCl

12

To a solution of N-ethylenediamine TFA salt (2.3 g, 7.0 mmol) in water 120 mL) at 60 C was added aqueous formaldehyde (0.72 g, 37% wt in water, 8.8 mmol, 1.26 equivs) over a period of 2.0 h. After 19 h at 60° C., it was cooled to ambient temperature. To the reaction mixture sodium hydroxide (0.38 g) and isopropyl acetate (20 mL) was added. The layers were separated and the aqueous layer was extracted with isopropyl acetate (10 mL). The organic layers were combined and washed with water (10 mL). To the organic layer was added conc. HCl (0.82 g) drop wise. The solids were filtered and washed with isopropyl acetate (5 mL). The crude product (2.44 g) was heated to 70° C. in ethanol (14 ml, 200 proof, denatured with 4% ethyl acetate) and then water (1.0 ml) was added. The solution was cooled to 5° C. over 3 hours. The product was filtered and washed with cold ethanol (2.4 mL). The wet product (1.4 g) was dried in a vacuum oven for 20 hours at 40° C. to afford the title compound (1.1 g, yield 60%) as a white solid. A second crop of 0.34 g (18%) was isolated from the mother liquor. HPLC (area %): 96.5%; Chiral purity (HPLC): 99.87:0.13

We claim:
1. A method for preparing a compound of formula II:

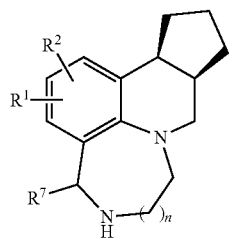

II or a pharmaceutically acceptable salt thereof, wherein:
n is 1;
$R^1$ and $R^2$ are each independently halogen, —CN, phenyl, —R, —OR, —$C_{1-6}$ perfluoroalkyl, or —$OC_{1-6}$ perfluoroalkyl;
each R is independently hydrogen or a $C_{1-6}$ alkyl group; and
$R^7$ is hydrogen or $C_{1-6}$ alkyl, comprising the steps of:
(a) providing a compound of formula E

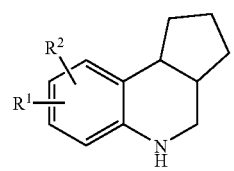

E wherein:
$R^1$ and $R^2$ are each independently halogen, —CN, phenyl, —R, —OR, —$C_{1-6}$ perfluoroalkyl, or —$OC_{1-6}$ perfluoroalkyl; and
each R is independently hydrogen or a $C_{1-6}$ alkyl group,
(b) treating said compound of formula E with a chiral agent to form a compound of formula D-1:

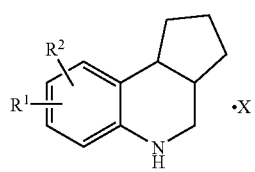

D-1 wherein:
$R^1$ and $R^2$ are each independently halogen, —CN, phenyl, —R, —OR, —$C_{1-6}$ perfluoroalkyl, or —$OC_{1-6}$ perfluoroalkyl;
each R is independently hydrogen or a $C_{1-6}$ alkyl group; and
X is a chiral agent,
(c) obtaining a compound of formula D by suitable physical means:

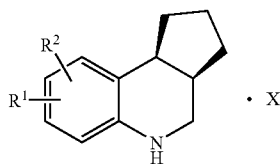

D wherein:
$R^1$ and $R^2$ are each independently halogen, —CN, phenyl, —R, —OR, —$C_{1-6}$ perfluoroalkyl, or —$OC_{1-6}$ perfluoroalkyl;
each R is independently hydrogen or a $C_{1-6}$ alkyl group; and
X is a chiral agent,
(d) treating said compound of formula D with a suitable base to provide a compound of formula C:

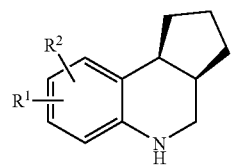

C wherein:
R¹ and R² are each independently halogen, —CN, phenyl, —R, —OR, —$C_{1-6}$ perfluoroalkyl, or —$OC_{1-6}$ perfluoroalkyl; and
each R is independently hydrogen or a $C_{1-6}$ alkyl group,
(e) alkylating said compound of formula C to form a compound of formula B:

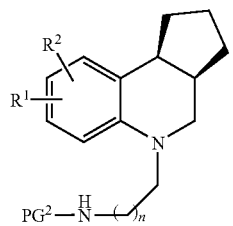

wherein:
n is 1;
R¹ and R² are each independently halogen, —CN, phenyl, —R, —OR, —$C_{1-6}$ perfluoroalkyl, or —$OC_{1-6}$ perfluoroalkyl;
each R is independently hydrogen or a $C_{1-6}$ alkyl group; and
PG² is a suitable amino protecting group,
(f) deprotecting said compound of formula B to form a compound of formula A

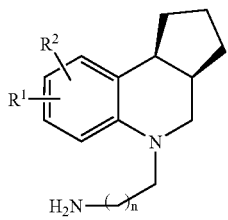

A wherein:
n is 1;
R¹ and R² are each independently halogen, —CN, phenyl, —R, —OR, —$C_{1-6}$ perfluoroalkyl, or —$OC_{1-6}$ perfluoroalkyl; and
each R is independently hydrogen or a $C_{1-6}$ alkyl group,
and
(g) reacting said compound of formula A with formaldehyde, or an equivalent thereof, to form a compound of formula II.

2. The method according to claim 1, wherein each n is 1 and R¹ and R² are both hydrogen.

3. The method according to claim 1, wherein said formaldehyde is aqueous formaldehyde.

4. The method according to claim 1, wherein the alkylation at step (e) is achieved by reacting said compound of formula C with

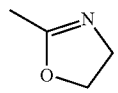

in the presence of a suitable acid to form a compound of formula B:

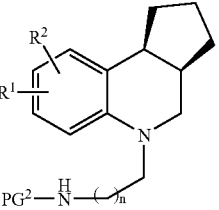

B wherein n is 1 and PG² is acetyl.

* * * * *